United States Patent
Kinoshiro et al.

(10) Patent No.: US 8,900,874 B2
(45) Date of Patent: Dec. 2, 2014

(54) METHOD AND DEVICE FOR ANALYZING SULFUR IN METAL SAMPLE

(75) Inventors: Satoshi Kinoshiro, Tokyo (JP); Kazutoshi Hanada, Tokyo (JP); Kyoko Fujimoto, Tokyo (JP)

(73) Assignee: JFE Steel Corporation, Tokyo (JP)

( * ) Notice: Subject to any disclaimer, the term of this patent is extended or adjusted under 35 U.S.C. 154(b) by 0 days.

(21) Appl. No.: 13/579,989

(22) PCT Filed: Feb. 17, 2011

(86) PCT No.: PCT/JP2011/000892
§ 371 (c)(1),
(2), (4) Date: Oct. 22, 2012

(87) PCT Pub. No.: WO2011/102137
PCT Pub. Date: Aug. 25, 2011

(65) Prior Publication Data
US 2013/0196445 A1    Aug. 1, 2013

(30) Foreign Application Priority Data

Feb. 18, 2010 (JP) ................................ 2010-033984

(51) Int. Cl.
*G01N 33/20* (2006.01)
*G01N 21/64* (2006.01)
*G01N 31/12* (2006.01)

(52) U.S. Cl.
CPC ............ *G01N 33/203* (2013.01); *G01N 21/643* (2013.01); *G01N 31/12* (2013.01)
USPC ................................ 436/123; 422/80; 422/50

(58) Field of Classification Search
CPC ...... G01N 33/203; G01N 33/20; G01N 33/00
USPC ....................................... 436/123; 422/80, 50
See application file for complete search history.

(56) References Cited

U.S. PATENT DOCUMENTS

| 3,529,937 A |   | 9/1970 | Ihari et al. |
|---|---|---|---|
| 4,582,686 A |   | 4/1986 | Tsuji |
| 5,424,217 A | * | 6/1995 | Benner et al. ................. 436/123 |
| 7,244,395 B2 | * | 7/2007 | Olstowski ....................... 422/80 |

FOREIGN PATENT DOCUMENTS

| CN | 101532960 | 9/2009 |
|---|---|---|
| JP | 49-043919 | 11/1974 |
| JP | 59-083054 | 5/1984 |
| JP | 59-099256 | 6/1984 |
| JP | 3-54461 | 3/1991 |
| JP | 06-138116 | 5/1994 |
| JP | 2000-28581 | 1/2000 |
| JP | 2000-88780 | 3/2000 |
| JP | 2003-065958 | 3/2003 |
| KR | 1990-0001569 | 3/1990 |
| RU | 2 352 933 | 4/2009 |
| WO | 2007/106094 | 9/2007 |

OTHER PUBLICATIONS

Syty Augusta, Determination of Sulfur Dioxide by Ultraviolet Absorption Spectrometry, Analytical Chemistry, vol. 45, No. 9, Aug. 1973, p. 1744-1747.*
Extended European Search Report dated Jun. 12, 2013 issued by the European Patent Office in corresponding European Patent Application No. 11744428.1, 4 pages.
International Search Report, PCT/JP2011/000892, Apr. 12, 2011.
Chinese Official Action—201180014323—Mar. 20, 2014.

\* cited by examiner

*Primary Examiner* — Christine T Mui
(74) *Attorney, Agent, or Firm* — Young & Thompson

(57) ABSTRACT

An analyzing method which enables highly precise and rapid quantitative analysis of sulfur contained in a metal sample, includes: combusting a metal sample containing a sulfur component under pure oxygen gas atmosphere to oxidize the sulfur component into sulfur dioxide; and quantitatively analyzing sulfur in the metal sample through analysis, according to a UV fluorescence method, of a sulfur dioxide containing gas containing the sulfur dioxide generated by combustion of the metal sample.

17 Claims, 7 Drawing Sheets

METHOD AND DEVICE FOR ANALYZING SULFUR IN METAL SAMPLE

TECHNICAL FIELD

The present invention relates to a method for analyzing sulfur in a metal sample and a device for implementing the method. In particular, the present invention relates to a sulfur-analyzing method suitable for quantitative analysis of sulfur contained in a metal sample made of steel, copper alloy or the like and a sulfur-analyzing device for implementing the method.

PRIOR ART

It is generally known that a sulfur component contained in a metal material such as copper alloy, steel or the like causes various effects on properties of the metal material. Specifically, it is known that a sulfur component contained in copper alloy significantly deteriorates hot formability of the copper alloy and a sulfur component contained in steel deteriorates toughness of the steel.

Therefore, it has been practiced in the steel industry in particular to adjust components of a metal material during refining thereof, based on an analytical value of sulfur content in the metal material, in order to obtain desired characteristics in the metal material. In view of this, there has been a demand for a method which enables highly precise and quick quantitative analysis of sulfur in a metal material, which method is applicable as method for analyzing sulfur in a metal material to such component adjustment during refining process as described above.

Examples of the conventional, known method for analyzing sulfur contained in steel include: wet process such as methylene blue spectrophotometry; and instrumental analysis such as infrared absorption method after combustion, spark source atomic emission spectrochemical analysis, and the like. Infrared absorption method after combustion, which is excellent in terms of accuracy of analytical values particularly when sulfur content in steel is significantly low (a few ppm) or high (several thousand ppm), is widely employed as a method for analyzing a sulfur component in the midst of production (refining) process of steel.

Infrared absorption method after combustion described above is a method for quantitative analysis of sulfur (S) in a sample, including the steps of combusting the sample in oxygen flow in a heating furnace such as an electric heating furnace or a high frequency induction heater and then introducing sulfur dioxide generated by the combustion of the sample into an infrared detector to measure absorbance of infrared having a wavelength corresponding to sulfur dioxide.

On the other hand, examples of the method for accurate quantitative analysis of sulfur contained in a petroleum product or a liquid organic synthetic material other than a metal material include sulfur analysis by the UV fluorescence method, which is a method for quantitatively analyzing sulfur in a sample by: decomposing by combustion a sample containing a sulfur component in a heating furnace under the supply of inert gas and oxygen, while controlling the gas flow rate and the oxygen concentration are kept constant before and after combustion of the sample; and measuring fluorescence intensity of sulfur dioxide in a resulting combustion gas by a UV fluorescence detector (see, for example, JP-A 2003-065958).

However, the conventional infrared absorption method after combustion described above has a problem in that analysis cannot be carried out rapidly because the analysis at the infrared detector is time-consuming Further, the aforementioned conventional infrared absorption method after combustion has additional problems in that: a dehumidifier, a gas flow rate adjusting device, and an adsorption and condensation column for trapping sulfur dioxide (a trap) must be provided between the heating furnace and the infrared detector in order to remove moisture and enhance analysis precision through reduction of noise; the gas to be analyzed cannot be fed at a high flow rate, in terms of ensuring satisfactory performance of the dehumidifier and the trap, whereby it takes time for sulfur dioxide generated by combustion of the sample to be introduced into the infrared detector and the analysis of sulfur content cannot be carried out quickly; and sulfur dioxide tends to remain in the analyzer, thereby possibly affecting the analysis results of the next sample. Further, a column filled with a hygroscopic reagent as particles each having particle diameter of 1 mm or less is generally used as a dehumidifier. However, the dehumidifier filled with such a hygroscopic reagent as described above exhibits quite poor gas permeability and a gas to be analyzed cannot be fed through the dehumidifier at a satisfactorily high flow rate. Besides, there is a possibility that sulfur dioxide in the gas to be analyzed is adsorbed by the hygroscopic reagent in the dehumidifier because sulfur dioxide is an easily-adsorbed material. That is, the conventional infrared absorption method after combustion has a critical problem in that a dehumidifier thereof, which is essentially required therein, tends to adversely affect analysis results of samples.

The conventional UV fluorescence method, in which a combustion tube for heating sample at relatively low temperature in the range of 1000° C. to 1100° C. is used in a heating furnace and inert gas must be supplied at a predetermined flow rate to keep oxygen concentration constant, has a problem that a metal sample, which must be combusted at high temperature, e.g. 1500° C. or higher, at relatively high oxygen concentration, cannot be analyzed in a sufficiently rapid and highly precise manner, although the method can well analyze an inflammable material such as a petroleum product.

DISCLOSURE OF THE INVENTION

Problems to be Solved by the Invention

In view of the situation described above, there has been a demand for developing an analyzing method and an analyzing device which enable highly precise and sufficiently rapid quantitative analysis of sulfur (S) contained in a metal sample.

Means for solving the Problem

The present invention aims at advantageously solving the problems described above. Specifically, a method for analyzing sulfur in a metal sample of the present invention, comprises: heating process of combusting a metal sample containing a sulfur component under pure oxygen gas atmosphere by high-frequency induction heating to oxidize the sulfur component into sulfur dioxide; and analyzing process of quantitatively analyzing sulfur in the metal sample through analysis, according to a UV fluorescence method, of a sulfur dioxide containing gas containing the sulfur dioxide generated by combustion of the metal sample. In the present invention, "pure oxygen gas" represents a gas of which oxygen concentration is at least 99.5 vol. %. Further, oxygen concentration can be measured by a paramagnetic oxygen analyzer in the present invention.

The heating process preferably involves high-frequency induction heating in the present invention because high-frequency induction heating enables rapid melting of a metal sample and facilitates generation of $SO_2$ due to self-stirring of molten metal by electromagnetic force. "High frequency" represents a frequency equal to or higher than 1 MHz in the present invention. Further, in the method for analyzing sulfur in a metal sample of the present invention, the proportion of oxygen gas with respect to the sulfur dioxide containing gas generated by the heating process is preferably at least 90 vol. % because then quantitative analysis of sulfur in a metal sample can be carried out in a more precise manner.

Further, in the method for analyzing sulfur in a metal sample of the present invention, the pure oxygen gas is preferably supplied at a flow rate of 4 L/min to 10 L/min in the heating process because quantitative analysis of sulfur in a metal sample can be carried out in a further more precise manner by combusting the metal sample under the supply of the pure oxygen gas at a flow rate of 4 L/min to 10 L/min Yet further, the method for analyzing sulfur in a metal sample of the present invention preferably further comprises: $SO_2$-containing gas flow rate measuring process of measuring a flow rate of the sulfur dioxide containing gas; and correction process of correcting, based on the flow rate of the sulfur dioxide containing gas measured by the $SO_2$-containing gas flow rate measuring process, a quantitative value of sulfur obtained by the analyzing process so as to eliminate an influence of variation in the flow rate of the sulfur dioxide containing gas.

Yet further, a device for analyzing sulfur in a metal sample of the present invention, comprises: pure oxygen gas supply means for supplying pure oxygen gas; a heating furnace for combusting a metal sample containing a sulfur component under atmosphere of the pure oxygen gas supplied by the pure oxygen gas supply means, to oxidize the sulfur component into sulfur dioxide; and a UV fluorescence analyzer for quantitatively analyzing sulfur in the metal sample by analyzing according to UV fluorescence method a sulfur dioxide containing gas containing the sulfur dioxide generated by combustion of the metal sample.

The heating furnace of the present invention is preferably a high-frequency induction heater because high-frequency induction heating enables rapid melting of a metal sample and facilitates generation of $SO_2$ due to self-stirring of molten metal by electromagnetic force.

Further, in the device for analyzing sulfur in a metal sample of the present invention, the pure oxygen gas supply means preferably includes $O_2$ gas-flow rate controlling means for controlling a supply flow rate of the pure oxygen gas. The pure oxygen gas supply means, when it is provided with the $O_2$ gas-flow rate controlling means, can adjust oxygen concentration in the sulfur dioxide containing gas to enable carrying out highly precise quantitative analysis of sulfur in a metal sample.

Yet further, the device for analyzing sulfur in a metal sample of the present invention preferably further comprises: $SO_2$-containing gas flow rate measuring means for measuring a flow rate of the sulfur dioxide containing gas; and correction means for correcting, based on the flow rate of the sulfur dioxide containing gas measured by the $SO_2$-containing gas flow rate measuring means, a quantitative value of sulfur obtained by the UV fluorescence analyzer so as to eliminate an influence of variation in the flow rate of the sulfur dioxide containing gas.

Effect of the Invention

According to the analyzing method and the analyzing device of the present invention, quantitative analysis of sulfur contained in a metal sample can be carried out highly precisely and rapidly.

BEST EMBODIMENT FOR CARRYING OUT THE INVENTION

Hereinafter, an embodiment of the present invention will be described in detail with reference to the drawings. Although a high-frequency induction heater is exemplarily shown as a heating furnace in the present embodiment, a heating furnace of any other type can be used as long as the heating furnace has heating capacity equivalent to that of a high-frequency induction furnace. Accordingly, the heating furnace of the present invention is not limited to a high-frequency induction heater. A UV fluorescence analyzing device 1 as one example of the analyzing device of the present invention is provided for quantitatively analysis of sulfur contained in a metal sample. Examples of the metal sample to be analyzed by the UV fluorescence analyzing device 1 include samples made of copper alloy, steel and the like, each containing a sulfur component by (sulfur-converted) content of 300 mass ppm or less (preferably 20 mass ppm or less).

Figure 1:
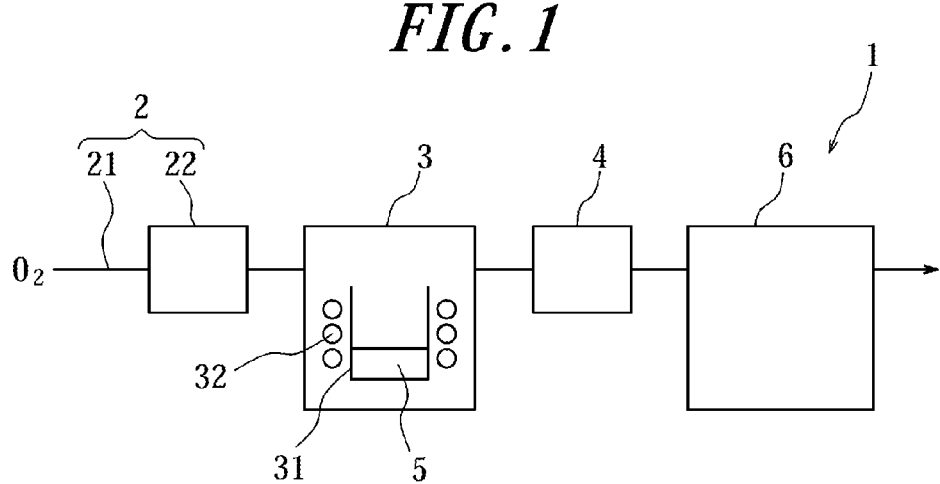
FIG. 1 is an explanatory view for explaining one example of structure of an analyzing device according to the present invention.

In the present embodiment, the UV fluorescence analyzing device 1 includes as shown in FIG. 1: a pure oxygen gas supply means 2; a high-frequency induction heater 3 for combusting a metal sample 5 under atmosphere of pure oxygen gas supplied by the pure oxygen gas supply means 2 to oxidize a sulfur component contained in the metal sample 5 into sulfur dioxide; a dust filter 4 for removing dust from sulfur dioxide containing gas generated by combustion of the metal sample 5 in the high-frequency induction heater 3; and a UV fluorescence analyzer 6 for quantitatively analyzing sulfur in the metal sample 5 by analyzing according to UV fluorescence method the sulfur dioxide containing gas from which dust has been removed.

The pure oxygen gas supply means 2 includes a pure oxygen gas (a gas having oxygen concentration of at least 99.5 vol. %) supply source (not shown), a pure oxygen gas supply line 21, and a flow rate adjusting device 22 as a flow rate controlling means provided on the pure oxygen gas supply line 21. Any known flow rate adjuster can be used as the flow rate adjusting device 22. A mass flow rate adjusting device capable of adjusting a mass flow rate of pure oxygen gas is preferably used as the flow rate adjusting device 22 in terms of ensuring good accuracy of the supply flow rate.

A ceramic crucible 31 accommodating a metal sample 5 charged therein and a coil 32 surrounding the ceramic crucible 31 are provided inside the high-frequency induction heater 3. The coil 32 is connected to an AC power source (not shown). In the high-frequency induction heater 3, AC current at 10-20 MHz, for example, is applied to the coil 32 under an atmosphere of the pure oxygen gas supplied via the pure oxygen gas supply means 2, so that the metal sample 5 in the ceramic crucible 31 melts rapidly and the sulfur component contained in the metal sample 5 is reacted with the pure oxygen gas, i.e. the metal sample 5 is combusted, to generate sulfur dioxide gas. A combustion improver such as tin, tungsten or the like is preferably used when the metal sample 5 is combusted. Charging the combustion improver, together with the metal sample 5, into the ceramic crucible 31 facilitates combustion of the metal sample 5 in high-frequency induction heating, thereby facilitating the whole process of quantitative analysis of sulfur in the metal sample 5.

The dust filter 4, provided between the high-frequency induction heater 3 and the UV fluorescence analyzer 6, functions to remove dust derived from the metal sample 5 and the combustion improver from the sulfur dioxide containing gas containing $SO_2$ generated in the high-frequency induction heater 3, to protect the downstream UV fluorescence analyzer 6. Examples of a material which can be used for the dust filter 4 include a material which does not adsorb sulfur dioxide, e.g. an air-breathable filter made of silicon fiber, polytetrafluoroethylene and the like.

The UV fluorescence analyzer 6 is adapted to irradiate the sulfur dioxide containing gas with UV rays having wavelength of, e.g. 220 nm, and measure for a certain time magnitude of fluorescence (wavelength: 330 nm) emitted when sulfur dioxide exited by the UV irradiation returns to the ground state, and calculate the amount of sulfur contained in the metal sample 5 from the integrated value of measured intensities of fluorescence by using a calibration curve prepared in advance. Any known UV fluorescence analyzer, specifically, any known UV fluorescence analyzer having a UV generating source, a fluorescence detection cell in which the sulfur dioxide containing gas is irradiated with UV rays, and a photomultiplier tube (PMT) for measuring excitation ray can be used as the UV fluorescence analyzer 6.

In the present embodiment, quantitative analysis of sulfur contained in the metal sample 5 can be carried out by using the UV fluorescence analyzing device 1 as follows, for example.

First, the metal sample 5 and the combustion improver are charged into the ceramic crucible 31. Pure oxygen gas is continually supplied to the high-frequency induction heater 3 via the pure oxygen gas supply means 2 and AC current is applied to the coil 32, so that the metal sample 5 is combusted in an atmosphere of the pure oxygen gas. Sulfur dioxide containing gas, containing $SO_2$ generated by combustion of the metal sample 5, is fed through the dust filter to have dust therein removed and then analyzed by the UV fluorescence analyzer 6. That is, the amount of sulfur contained in the metal sample can be quantitatively analyzed from the amount of $SO_2$ generated by combustion of the metal sample 5.

According to the UV fluorescence analyzing device 1, the metal sample 5 can be rapidly and sufficiently combusted under an oxygen atmosphere by using the high-frequency induction heater 3. Further, the UV fluorescence analyzing device 1 is hardly affected by moisture and temperature of the gas to be analyzed, as compared with the conventional technique measuring sulfur dioxide by an infrared detector, because the UV fluorescence analyzing device 1 measures sulfur dioxide, generated by combustion of the metal sample 5, by the UV fluorescence analyzer 6. That is, the UV fluorescence analyzing device 1 enables rapid and accurate quantitative analysis of sulfur with a simple device without provision of a dehumidifier, a flow rate adjusting device provided between the dehumidifier and the infrared detector, and an adsorption and condensation column (a trap) for trapping $SO_2$. Further, the UV fluorescence analyzing device 1 does not necessitate use of a reference gas (a comparison gas), which is essentially required in the conventional technique.

Oxygen generally absorbs fluorescence emitted when sulfur dioxide in the excited state returns to the ground state and also collides with sulfur dioxide molecules in the excited state to cause "quenching" phenomenon, thereby possibly deteriorating precision of $SO_2$ concentration measurement when $SO_2$ concentration in the gas to be analyzed is significantly low and/or oxygen content in the gas to be analyzed is very high in particular in a case where the measurement is carried out by the UV fluorescence method. However, the UV fluorescence analyzing device 1 can avoid such problems as described above of the conventional UV fluorescence analyzer and enables accurate measurement of $SO_2$ concentration because the UV fluorescence analyzing device 1 employs the high-frequency induction heater 3 capable of combusting a metal sample rapidly, thereby ensuring complete oxidization of sulfur in the metal sample in a relatively short time and satisfactorily high $SO_2$ concentration in the gas to be analyzed and thus successfully obtaining a point-headed, sharp peak in fluorescence intensity measured by the UV fluorescence analyzer 6.

Oxygen causes an effect of quenching fluorescence of sulfur dioxide as described above and therefore it is known that different fluorescence intensities may be detected when gases having the same $SO_2$ concentration and different $O_2$ concentrations are analyzed as $SO_2$-containing gases by the UV fluorescence method. Further, it is known that, when a metal sample is combusted, oxygen is bonded to not only the metal itself and a sulfur component in the metal sample but also hydrogen, carbon and the like therein, thereby generating non-oxygen gas(es) other than $SO_2$ gas.

Therefore, it is preferable to supply pure oxygen gas such that oxygen concentration in the sulfur dioxide containing gas is at least 90 vol. %, i.e. difference in oxygen concentration between gas supplied to the high-frequency induction heater 3 (pure oxygen gas) and the sulfur dioxide containing gas is not larger than 10 vol. % in the UV fluorescence analyzing device 1. Specifically, pure oxygen gas is preferably supplied at a flow rate of, e.g. 4 L/min to 10 L/min to the high-frequency induction heater 3. $O_2$ concentration in the $SO_2$ containing gas can reliably remain at least 90 vol. % and variation in oxygen concentration is significantly prevented from affecting fluorescence intensity, thereby ensuring accurate measurement of sulfur dioxide, by supplying pure oxygen gas at a flow rate of 4 L/min to 10 L/min to the high-frequency induction heater 3, even if the $O_2$ concentration in the $SO_2$ containing gas is somewhat lower than the $O_2$ concentration of the pure oxygen gas supplied to the high-frequency induction heater 3 due to presence of non-oxygen gas(es) generated by combustion of the metal sample 5. More specifically, when pure oxygen gas is supplied to the high-frequency induction heater 3 at a flow rate of at least 4 L/min, time required for $SO_2$ generated in the high-frequency induction heater 3 to reach the UV fluorescence analyzer 6 and thus overall time required for the analysis is reliably shortened and $SO_2$ generated in the UV fluorescence analyzing device 1 is reliably prevented from remaining within the analyzer. When pure oxygen gas is supplied to the high-frequency induction heater 3 at a flow rate of 10 L/min or less, the dust filter 4 will be less frequently clogged up with dust than otherwise and cost and labor for maintenance of the device can be significantly reduced.

The analyzing device of the present invention is not restricted to the aforementioned example and any change can be made thereto in an appropriate manner. Specifically, the analyzing device of the present invention may further include: $SO_2$-containing gas flow rate measuring means for measuring a flow rate of the sulfur dioxide containing gas generated by combustion of the metal sample, provided on the downstream side of the high-frequency induction heater, i.e. between the high-frequency induction heater and the UV fluorescence analyzer or on the downstream side of the UV fluorescence analyzer; and correction means for correcting, based on the flow rate of the sulfur dioxide containing gas measured by the $SO_2$-containing gas flow rate measuring means, a quantitative value of sulfur obtained by the UV fluorescence analyzer. That is, the analyzing device of the present invention may have structure as shown in FIG. 2.

Figure 2:
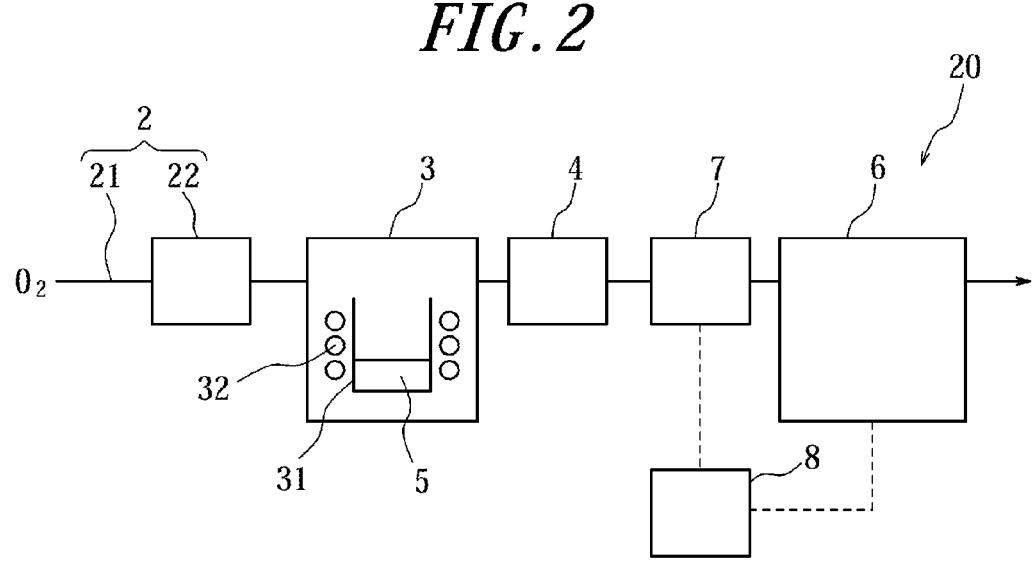
FIG. 2 is an explanatory view for explaining another example of structure of the analyzing device according to the present invention.

A UV fluorescence analyzing device 20 as another example of the analyzing device of the present invention, shown in FIG. 2, has the same structure as the UV fluorescence analyzing device 1 of the aforementioned example, except that the former includes a flowmeter 7 as the $SO_2$-containing gas flow rate measuring means between the dust filter 4 and the UV fluorescence analyzer 6 and a computer 8 as the correction means electrically connected to the UV fluorescence analyzer 6 and the flowmeter 7, respectively.

Examples of a flowmeter which can be used as the flowmeter 7 include any flowmeter capable of measuring a volume flow rate of the $SO_2$ containing gas such as an orifice flowmeter, a vortex flowmeter, a float-type flowmeter and the like. Specifically, in a case where oxygen concentration in the $SO_2$ containing gas is relatively high, e.g. at least 90 vol. %, an oxygen flowmeter may be used as the flowmeter 7 in the analyzing device of the present invention, to regard a flow rate measured by the oxygen flowmeter as a flow rate of the $SO_2$ containing gas. In this case, a mass flowmeter such as a hot wire flowmeter, a coriolis mass flowmeter, or the like may be used as the flowmeter 7.

The computer 8 is adapted to correct, based on the flow rate of the sulfur dioxide containing gas measured by the flowmeter 7, a quantitative value of sulfur obtained by the UV fluorescence analyzer 6 so as to eliminate an influence of variation in the flow rate of the sulfur dioxide containing gas. In the present invention, examples of a method for correcting a quantitative value of sulfur to eliminate an influence of variation in the flow rate of the sulfur dioxide containing gas therefrom include:

(1) a method having the steps of: obtaining a series of instantaneous values (I) of fluorescence intensity continuously or continually measured by the UV fluorescence analyzer 6 during the analysis of the metal sample 5, as well as a series of instantaneous values (Q) of flow rate of the $SO_2$ containing gas each measured synchronous with the corresponding instantaneous value (I); calculating a coefficient (Q/q) by dividing each Q by a given reference flow rate (q); multiplying respective instantaneous values (I) by the corresponding coefficients (Q/q) to obtain a series of the corrected instantaneous values (I') of fluorescence intensity (i.e. I'=I×Q/q); and integrate the corrected instantaneous values (I') to obtain a corrected quantitative value of sulfur; and (2) a method having the steps of: calculating an integrated value (ΣI) by integrating a series of the instantaneous values (I) of fluorescence intensity; calculating a coefficient (Qm/q) by dividing the average flow rate (Qm) of the $SO_2$ containing gas being analyzed, by a given reference flow rate (q); multiplying the integrate value (ΣI) by the coefficient (Qm/q) to obtain the corrected integrated value (ΣI') of fluorescence intensity (i.e. ΣI'=ΣI×Qm/q); and determining a corrected quantitative value of sulfur from the corrected integrated value (ΣI') of fluorescence intensity.

Any appropriate flow rate can be used as the reference flow rate (q). For example, the value (q) may be equal to 1 or equal to the supply flow rate of pure oxygen gas to the UV fluorescence analyzing device 20.

Figure 5:
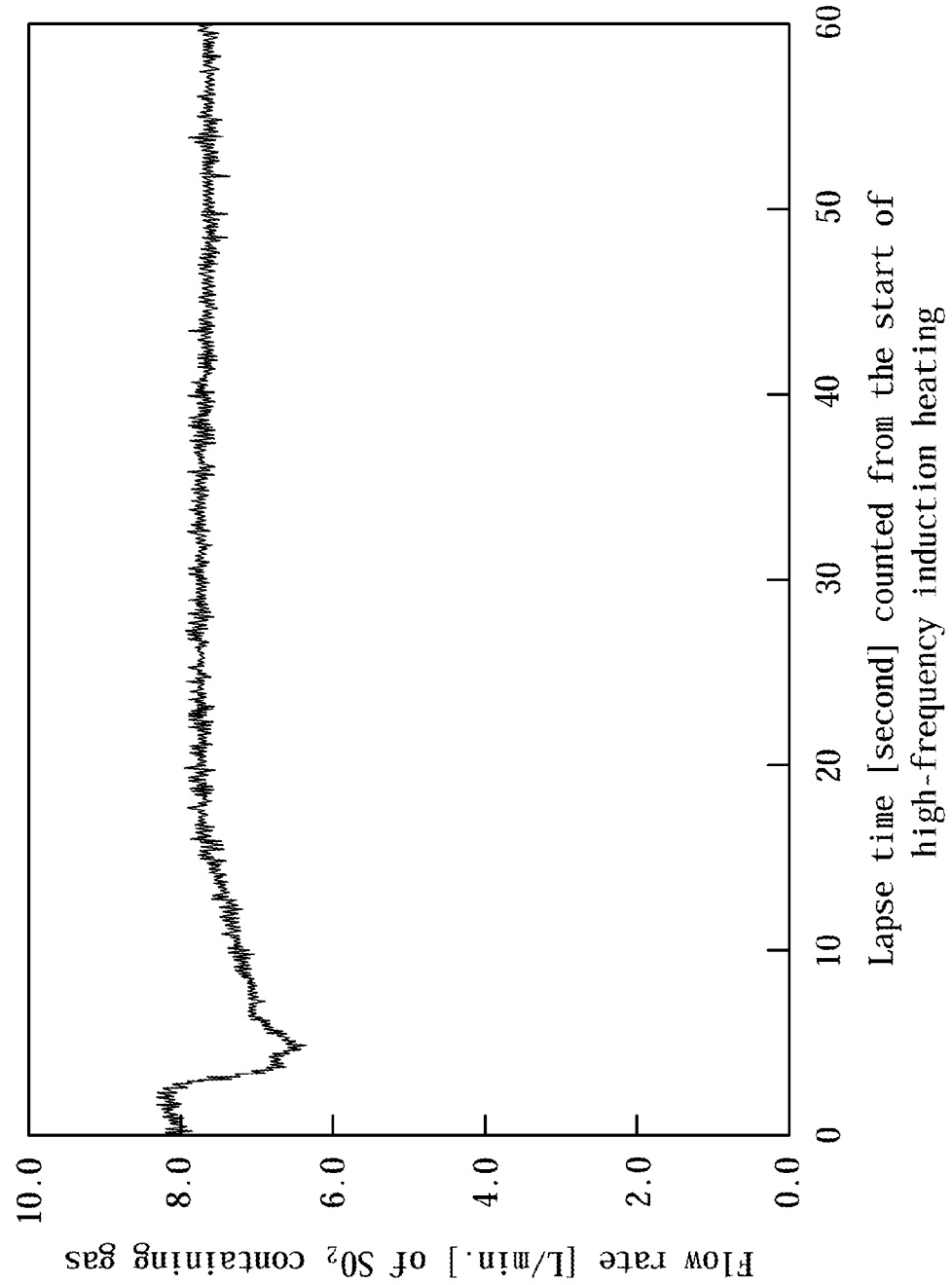
FIG. 5 is a graph showing relationship between lapse time counted from the start of high-frequency induction heating vs. flow rate of $SO_2$ containing gas generated by combustion when a metal sample is combusted in a high-frequency induction heater for sulfur analysis.
Figure 6:
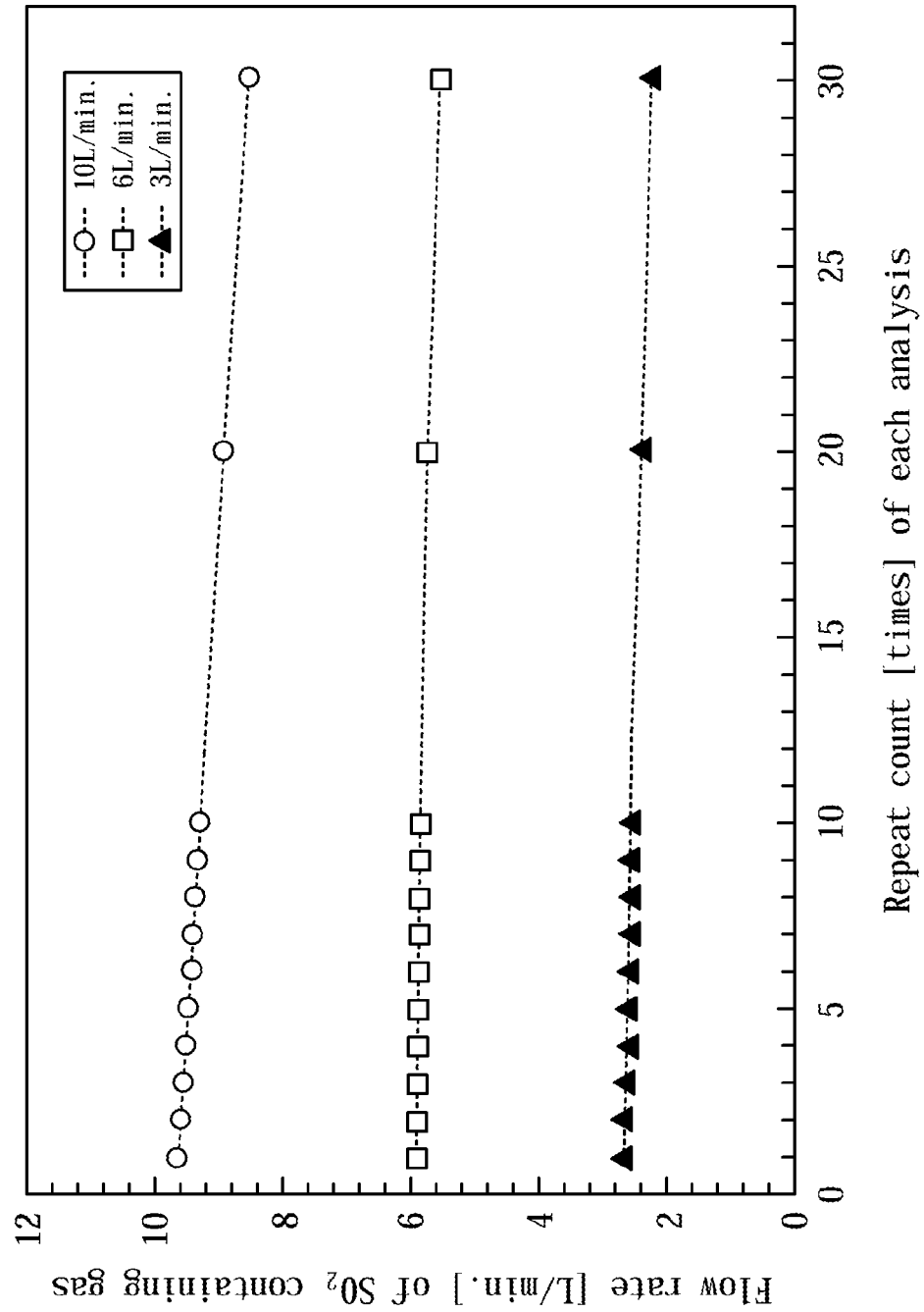
FIG. 6 is a graph showing relationship between the repeat count of each analysis vs. flow rate of $SO_2$ containing gas generated by combustion when a metal sample is combusted in a high-frequency induction heater for sulfur analysis.

It has been revealed as a result of a study made by the inventors of the present invention that variation in flow rate of gas to be analyzed significantly affects fluorescence intensity values measured by a UV fluorescence analyzer, whereby variation in flow rate of $SO_2$ containing gas during analysis possibly results in erroneous quantitative values of sulfur in the UV fluorescence method. The inventors of the present invention also discovered that in the UV fluorescence analyzing device 1 as shown in FIG. 1 a flow rate of $SO_2$ containing gas, generated by combustion of the metal sample 5 in the high-frequency induction heater 3, possibly changes over time during analysis as shown in FIG. 5. Further, the inventors of the present invention discovered after the repeated analyses that a flow rate of $SO_2$ containing gas tends to drop due to clogging-up of the dust filter 4 caused by repeated analysis, as shown in FIG. 6.

The UV fluorescence analyzing device 20 shown in FIG. 2 carries out correction by the computer 8 based on the flow rate of the $SO_2$-containing gas measured by the flowmeter 7 in view of a possibility of occurrence of errors as described above, whereby it is possible to eliminate an influence of errors caused by variation in gas flow rate during each analysis and discrepancy in gas flow rate between respective analyses in the UV fluorescence analyzing device 20. Accordingly, the UV fluorescence analyzing device 20 can achieve, in addition to the superior effect that it enables highly precise and rapid analysis, a superior effect that it can quantitatively analyze sulfur in a metal sample in a more accurate manner than the he UV fluorescence analyzing device 1.

Further, as is obvious from the foregoing embodiment, a metal sample is combusted under an atmosphere of pure oxygen gas by high-frequency induction heating according to the method for analyzing sulfur in a metal sample of the present invention, whereby it is possible to rapidly and sufficiently oxidize a sulfur component contained in the metal sample into sulfur dioxide. Yet further, a gas generated by combustion of the metal sample is analyzed according to the UV fluorescence method, whereby it is possible to carry out quantitative analysis of sulfur contained in the metal sample rapidly and highly precisely. Accordingly, the analyzing method of the present invention ensures highly precise and rapid quantitative analysis of sulfur contained in a metal sample.

Yet further, a metal sample is combusted under an atmosphere of pure oxygen gas by using a high-frequency induction heater according to the device for analyzing sulfur in a metal sample of the present invention, whereby it is possible to rapidly and sufficiently oxidize a sulfur component contained in the metal sample into sulfur dioxide. Yet further, a gas generated by combustion of the metal sample is analyzed according to the UV fluorescence method, whereby it is possible to carry out quantitative analysis of sulfur contained in the metal sample rapidly. As a result, rapid and highly precise quantitative analysis of sulfur contained in the metal sample can be carried out according to the analyzing device of the present invention.

EXAMPLE 1

The present invention will be described further in detail hereinafter by Example 1 where a steel material was used for samples to be analyzed. The present invention is not restricted by any means to this Example.

(Samples 1 to 5)

The steel standard sample JSS 244-6 (sulfur content: 20 mass ppm) was subjected to five different type of analyses (samples 1 to 5) by using the UV fluorescence analyzing device 1 shown in FIG. 1 under the respective conditions summarized in Table 1. Each analysis was repeated five times. The high-frequency induction heater portion of a carbon-sulfur analyzer EMIA-620 (manufactured by HORIBA Ltd.) was exclusively used as the high-frequency induction heater 3 and an ambient air sulfur dioxide analyzer GFS-352 (manufactured by DKK-TOA CORPORATION), which had been modified, was used as the UV fluorescence analyzer 6. Specifically, the ambient air sulfur dioxide analyzer GFS-352 (manufactured by DKK-TOA CORPORATION) was modified such that: it allowed pulse fluorescence signals generated by $SO_2$ to be collected, without being subjected to average processing in advance, for measurement of the maximum values of the respective pulses; and an internally installed pump was removed and gas flow control was carried out by a flow rate adjusting device 22.

Figure 7:
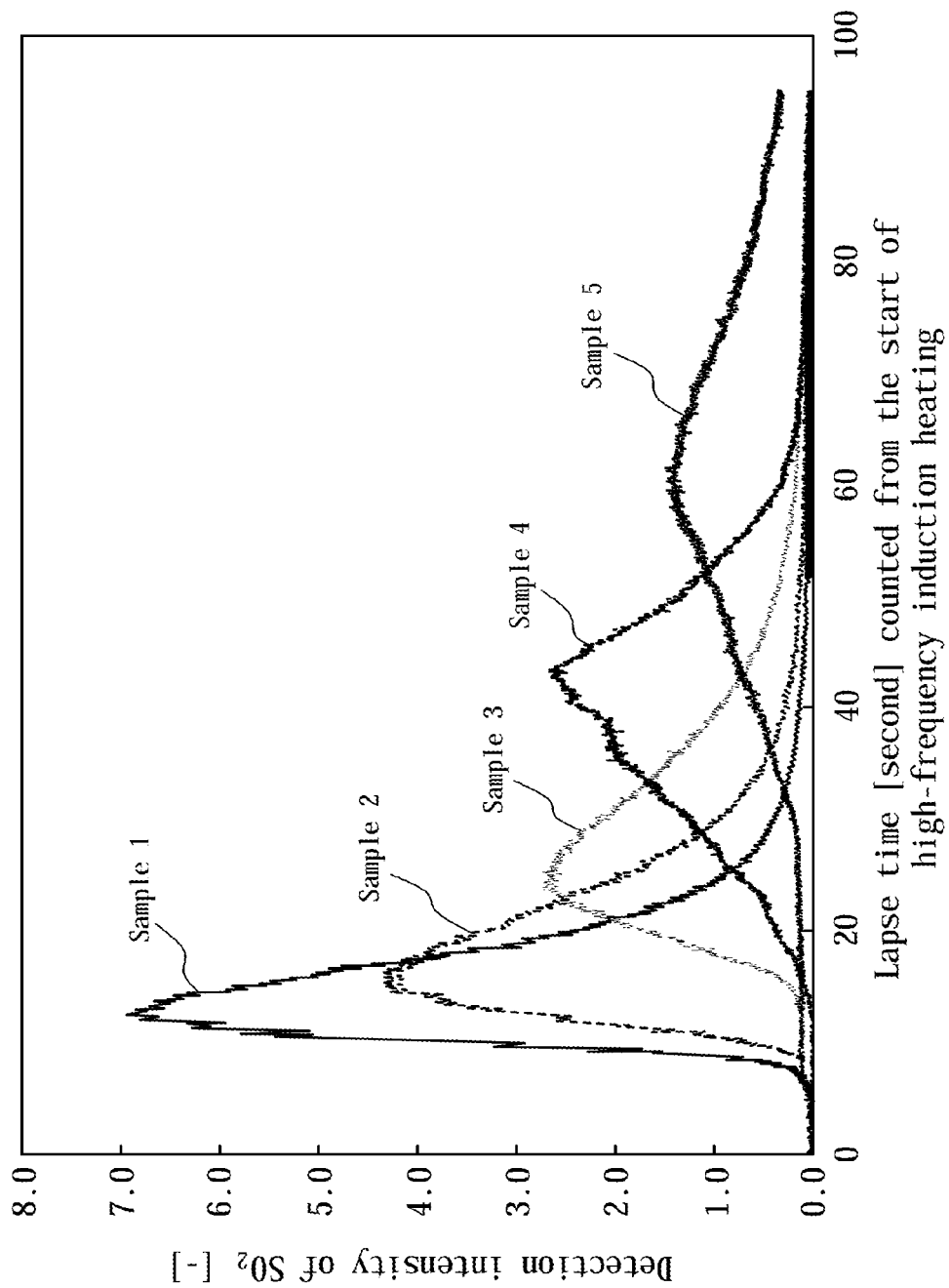
FIG. 7 is a graph showing relationships between lapse time counted from the start of high-frequency induction heating vs. detection intensity of $SO_2$ at a UV fluorescence analyzer when standard steel samples of the same type are analyzed by the analyzing device shown in FIG. 1 at variously changed composition of a gas supplied to the high-frequency induction heater.

Tungsten and tin were used as combustion improvers and gases having flow rates and compositions as shown in Table 1 were used, respectively, as the gas supplied to the high-frequency induction heater 3 in the analyses of samples 1 to 5. FIG. 7 shows for each of steel standard samples 1 to 5 the relationship between lapse time counted from the start of high-frequency induction heating vs. detection intensity of $SO_2$ at the UV fluorescence analyzer 6. The analysis time estimated from the graph of FIG. 7 and the standard deviation of sulfur content calculated from fluorescence intensity of sulfur dioxide detected by the UV fluorescence analyzer 6 are shown for each of samples 1 to 5 in Table 1.

TABLE 1

|  | Sample No. | | | | |
| --- | --- | --- | --- | --- | --- |
|  | Sample 1 | Sample 2 | Sample 3 | Sample 4 | Sample 5 |
| Sample weight [g] | 0.5 | 0.5 | 0.5 | 0.5 | 0.5 |
| Added amount of tungsten [g] | 1.2 | 1.2 | 1.2 | 1.2 | 1.2 |
| Added amount of tin [g] | 0.3 | 0.3 | 0.3 | 0.3 | 0.3 |
| Flow rate of gas supplied to high-frequency induction heater [L/min.] | 4.5 | 4.5 | 4.5 | 4.5 | 4.5 |
| Oxygen concentration in the gas supplied to high-frequency induction heater [vol. %] | 100 | 90 | 80 | 70 | 60 |
| Argon concentration in the gas supplied to high-frequency induction heater [vol. %] | 0 | 10 | 20 | 30 | 40 |
| Standard deviation of sulfur content [mass ppm] | 0.32 | 0.49 | 1.80 | 2.70 | 3.68 |
| Analyzing time [second] | 40 | 50 | 80 | 80 | at least 90 |
| Note | Example | Comp. Ex. | Comp. Ex. | Comp. Ex. | Comp. Ex. |

It is understood from the results of samples 1 to 5 shown in Table 1 and FIG. 7 that a phenomenon that sulfur dioxide at a very low concentration continues to be detected over a relatively long period (what is called "tailing") is significantly prevented from occurring in the analyzing device using pure oxygen as the supply gas of the present invention, whereby sulfur in a metal sample can be rapidly and highly precisely analyzed with little variation in measurement values according to the analyzing device of the present invention.

EXAMPLE 2

The present invention will be described further in detail hereinafter by Example 2 where a steel material was used for samples to be analyzed. The present invention is not restricted by any means to this Example.

(Samples 6 to 10)

Figure 8:
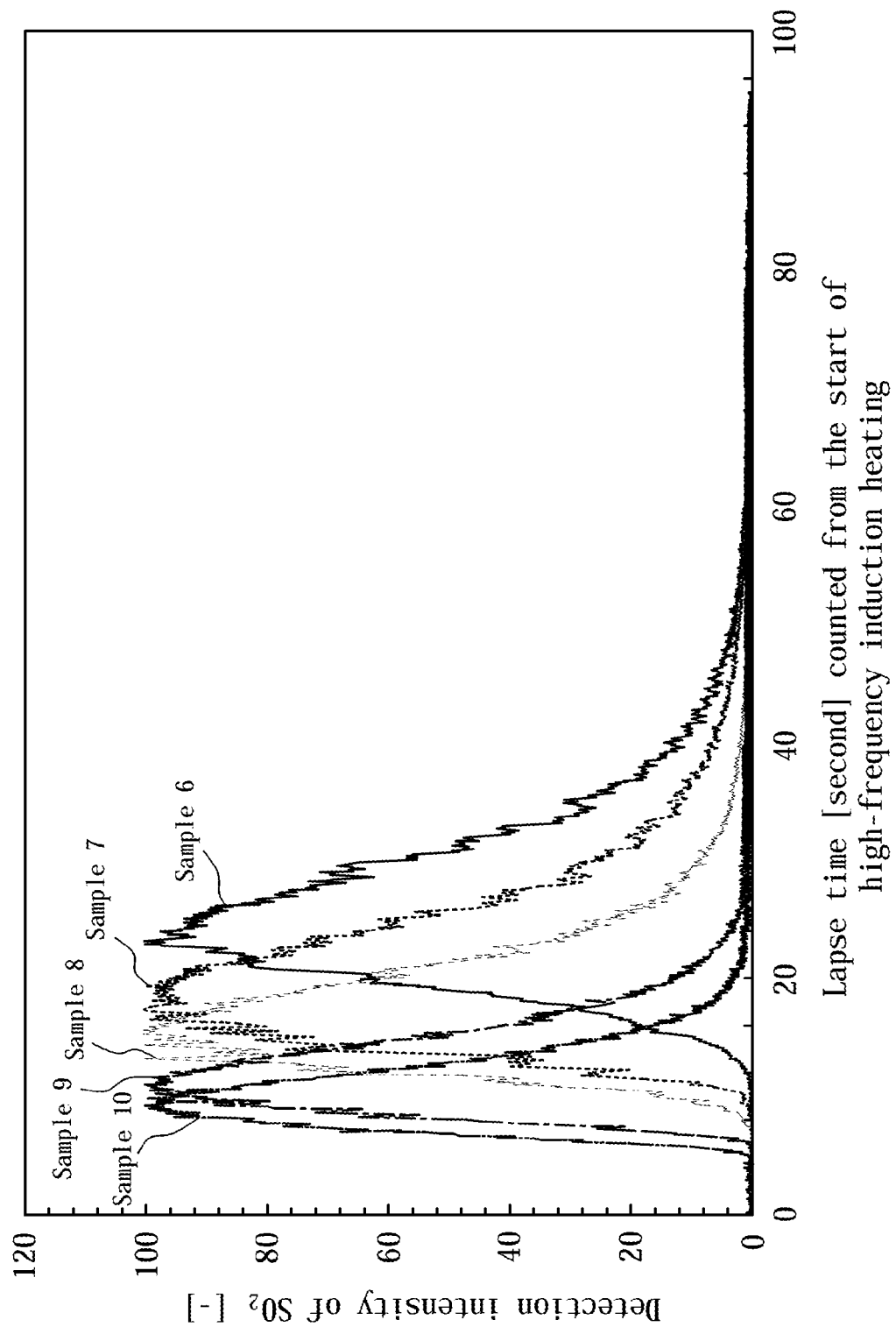
FIG. 8 is a graph showing relationships between lapse time counted from the start of high-frequency induction heating vs. detection intensity of $SO_2$ at a UV fluorescence analyzer when standard steel samples of the same type are analyzed by the analyzing device shown in FIG. 1 at variously changed flow rate of pure oxygen gas.

The steel standard sample JSS 244-6 (sulfur content: 20 mass ppm) was subjected to five different type of analyses (samples 6 to 10) by using the UV fluorescence analyzing device 1 shown in FIG. 1 in the same manner as in Example 1, except that pure oxygen was used as the gas supplied to the high-frequency induction heater 3 and the flow rate of the pure oxygen was changed under the respective conditions shown in Table 2. Each analysis was repeated five times. The standard deviation of sulfur content calculated from fluorescence intensity of sulfur dioxide detected by the UV fluorescence analyzer 6 and the time required for the analysis are shown for each of samples 6 to 10 in Table 2. Further, FIG. 8 shows for each of steel standard samples 6 to 10 the relationship between lapse time counted from the start of high-frequency induction heating vs. detection intensity of $SO_2$ at the UV fluorescence analyzer 6. Each $SO_2$ detection intensity value is expressed as an index value relative to the maximum value of the detected $SO_2$ fluorescence intensity being converted into 100.

(Sample 11)

Figure 3:
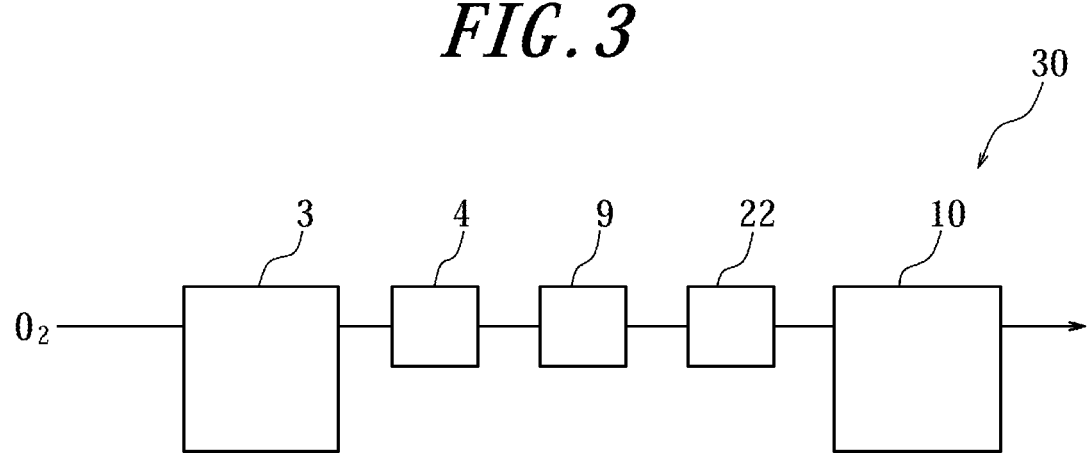
FIG. 3 is an explanatory view for explaining structure of an analyzing device of a Comparative Example.
Figure 9:
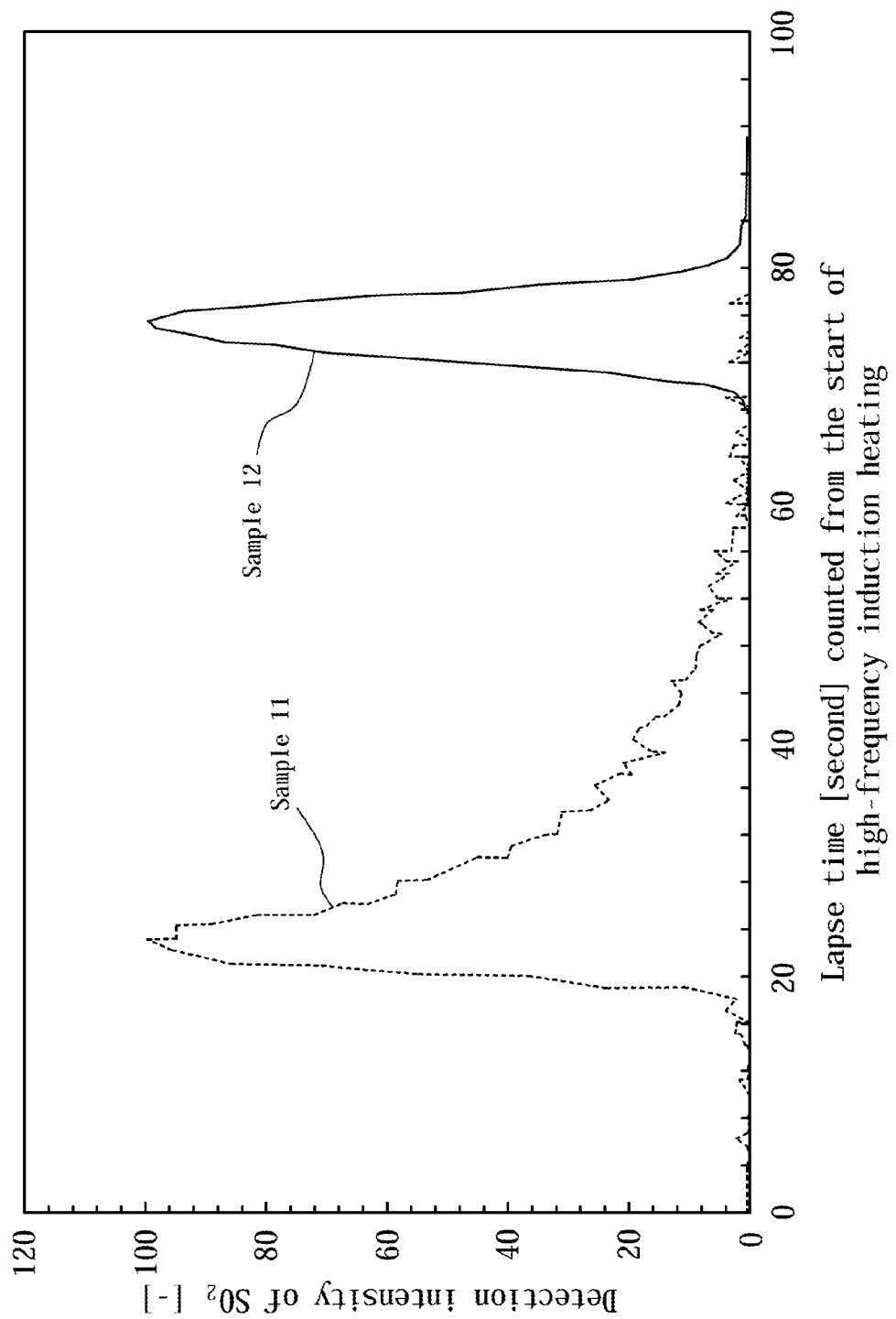
FIG. 9 is a graph showing relationships between lapse time counted from the start of high-frequency induction heating vs. detection intensity of $SO_2$ detected by an analyzer according to high-frequency infrared absorption method after combustion when standard steel samples of the same type are analyzed by the analyzing device shown in FIG. 3 and FIG. 4, respectively.

The steel standard sample JSS 244-6 was subjected to one type of analysis (sample 11), which was repeated five times, under an atmosphere of pure oxygen and the condition shown in Table 2 by using an analyzing device 30 according to the high-frequency infrared absorption after combustion (a carbon-sulfur analyzer EMIA-620, manufactured by HORIBA Ltd.) including the high-frequency induction heater 3, a dust filter 4, a dehumidifier 9, a flow rate adjusting device 22, and an IR detector 10 sequentially connected to each other in this order as shown in FIG. 3. Tungsten and tin were used as combustion improvers in the analyses of sample 11. The standard deviation of sulfur content calculated from absorbance intensity of sulfur dioxide detected by the IR detector 10 and the time required for the analysis, of sample 11, are shown in Table 2. Further, FIG. 9 shows the relationship between lapse time counted from the start of high-frequency induction heating vs. detection intensity of $SO_2$ at the IR detector 10 observed in steel standard sample 11. Each $SO_2$ detection intensity value is expressed as an index value relative to the maximum value of the $SO_2$ absorbance intensity being converted into 100 in FIG. 9.

(Sample 12)

Figure 4:
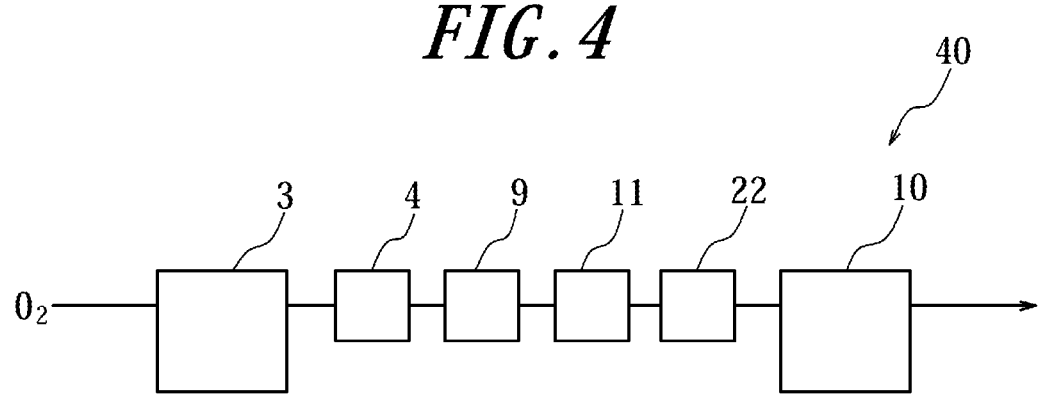
FIG. 4 is an explanatory view for explaining structure of an analyzing device of another Comparative Example.

The steel standard sample JSS 244-6 was subjected to one type of analysis (sample 12), which was repeated five times, under an atmosphere of pure oxygen and the condition shown in Table 2 by using an analyzing device 40 according to the high-frequency infrared absorption after combustion (CS-444LS, manufactured by LECO CORPORATION) including the high-frequency induction heater 3, a dust filter 4, a dehumidifier 9, a sulfur dioxide adsorption and condensation column 11, a flow rate adjusting device 22, and an IR detector 10 sequentially connected to each other in this order as shown in FIG. 4. Tungsten and tin were used as combustion improvers in the analyses of sample 12. The standard deviation of sulfur content calculated from absorbance intensity of sulfur dioxide detected by the IR detector 10 and the time required for the analysis, of sample 12, are shown in Table 2. Further, FIG. 9 shows the relationship between lapse time counted from the start of high-frequency induction heating vs. detection intensity of $SO_2$ at the IR detector 10 observed in steel standard sample 12. Each $SO_2$ detection intensity value is expressed as an index value relative to the maximum value of the $SO_2$ absorbance intensity being converted into 100 in FIG. 9.

EXAMPLE 3

The present invention will be described further in detail hereinafter by Example 3 where a steel material was used for samples to be analyzed. The present invention is not restricted by any means to this Example.

(Sample 13)

The steel standard sample JSS 244-6 was subjected to the same type of analysis as the analysis of sample 1, except that the UV fluorescence analyzing device 20 as shown in FIG. 2 was used, pure oxygen gas was supplied by the pure oxygen gas supply means 2 at the flow rate of 6 L/min, a flow rate of $SO_2$ containing gas generated by the high-frequency induction heater 3 was measured by the flowmeter 7, and the analysis was repeated consecutively by totally 30 times. Time required per one course of the analysis was 40 seconds. "SEF-21A", manufactured by HORIBA Ltd., was used as the flowmeter. Correction by the computer 8 was carried out by the method of multiplying the integrated value of a series of instantaneous values of fluorescence intensity by a coefficient obtained by dividing the average flow rate of the $SO_2$ containing gas being analyzed by the reference flow rate (6 L/min). Sulfur content calculated from the fluorescence intensity value which has been corrected by the computer 8, of sulfur dioxide detected by the UV fluorescence analyzer 6, and sulfur content derived from the fluorescence intensity value which has not been corrected by the computer 8, of sulfur dioxide detected by the UV fluorescence analyzer 6, are shown in Table 3 for the first, the tenth, the twentieth, and the thirtieth analysis. The standard deviation of sulfur content, calculated from fluorescence intensity values of sulfur dioxide detected by the UV fluorescence analyzer 6 in the first to the fifth analysis, was 0.14 mass ppm.

TABLE 3

|  | Repeat count of analysis | | | |
| --- | --- | --- | --- | --- |
|  | 1(st) | 10(th) | 20(th) | 30(th) |
| Sample weight [g] | 0.5 | 0.5 | 0.5 | 0.5 |
| Added amount of tungsten [g] | 1.2 | 1.2 | 1.2 | 1.2 |
| Added amount of tin [g] | 0.3 | 0.3 | 0.3 | 0.3 |
| Average flow rate of $SO_2$ containing gas [L/min.] | 5.91 | 5.85 | 5.72 | 5.52 |

TABLE 2

| Sample No. | Sample 6 | Sample 7 | Sample 8 | Sample 9 | Sample 10 | Sample 11 | Sample 12 |
| --- | --- | --- | --- | --- | --- | --- | --- |
| Sample weight [g] | 0.5 | 0.5 | 0.5 | 0.5 | 0.5 | 0.5 | 0.5 |
| Added amount of tungsten [g] | 1.2 | 1.2 | 1.2 | 1.2 | 1.2 | 1.2 | 1.2 |
| Added amount of tin [g] | 0.3 | 0.3 | 0.3 | 0.3 | 0.3 | 0.3 | 0.3 |
| Flow rate of pure oxygen [L/min.] | 2.5 | 3.0 | 4.0 | 7.0 | 10.0 | 2.5 | 2.5 |
| Standard deviation of sulfur content [mass ppm] | 0.52 | 0.47 | 0.30 | 0.18 | 0.20 | 1.20 | 0.32 |
| Analyzing time [second] | 60 | 60 | 40 | 30 | 20 | 60 | 85 |
| Note | Example | Example | Example | Example | Example | Comp. Ex. | Comp. Ex. |

It is understood from Table 2 and FIGS. 8 and 9 that occurrence of tailing is reliably prevented and quantitative analysis of sulfur in a metal sample can be carried out rapidly and highly precisely in the analyzing device of the present invention. Further, it is understood in particular that occurrence of tailing is reliably prevented and quantitative analysis of sulfur in a metal sample can be carried out rapidly and highly precisely by setting the flow rate of pure oxygen to be in the range of 4 L/min to 10 L/min.

TABLE 3-continued

|  | Repeat count of analysis | | | |
| --- | --- | --- | --- | --- |
|  | 1(st) | 10(th) | 20(th) | 30(th) |
| Uncorrected sulfur content [mass ppm] | 20.2 | 20.5 | 21.1 | 21.7 |
| Corrected sulfur content [mass ppm] | 19.9 | 20.0 | 20.1 | 20.0 |

It is understood from the results shown in Table 3 that accuracy of quantitative analysis of sulfur in a metal sample can be enhanced by measuring a flow rate of sulfur dioxide containing gas and making corrections based on the flow rate.

Industrial Applicability

According to the present invention, quantitative analysis of sulfur contained in a metal sample can be carried out rapidly and highly precise manner.

EXPLANATION OF REFERENCE NUMERALS

1 UV fluorescence analyzing device
2 Pure oxygen gas supply means
3 High-frequency induction heater
4 Dust filter
5 Metal sample
6 UV fluorescence analyzer
7 Flowmeter
8 Computer
9 Dehumidifier
10 IR detector
11 Sulfur dioxide adsorption and condensation column
20 UV fluorescence analyzing device
21 Pure oxygen gas supply line
22 Flow rate adjusting device
30 Analyzing device according to the high-frequency infrared absorption after combustion
31 Ceramic crucible
32 Coil
40 Analyzing device according to the high-frequency infrared absorption after combustion

The invention claimed is:

1. A method for analyzing sulfur in a metal sample, comprising:
heating and combusting a metal sample containing a sulfur component under a pure oxygen gas atmosphere to oxidize the sulfur component into sulfur dioxide, producing a sulfur dioxide containing gas from the combustion; and
quantitatively analyzing the sulfur dioxide in the sulfur dioxide containing gas according to a UV fluorescence method.

2. The method of claim 1, wherein the pure oxygen gas atmosphere comprises at least 99.5 vol. % of oxygen, and the heating comprises high-frequency induction heating.

3. The method of claim 1, wherein the proportion of oxygen gas with respect to the sulfur dioxide containing gas is at least 90 vol. %.

4. The method of claim 1, wherein during the heating and combusting the pure oxygen gas is supplied at a flow rate of 4 L/min. to 10 L/min.

5. The method of claim 1, further comprising:
measuring a flow rate of the sulfur dioxide containing gas; and
based on the measured flow rate of the sulfur dioxide containing gas, correcting a quantitative value of sulfur obtained by the analyzing process so as to eliminate an influence of variation in the flow rate of the sulfur dioxide containing gas.

6. A device for analyzing sulfur in a metal sample, comprising:
a heating furnace configured to combust a metal sample containing a sulfur component under an atmosphere of pure oxygen gas and oxidize the sulfur component into sulfur dioxide, producing a sulfur dioxide containing gas from the combustion;
a means for supplying pure oxygen gas to the heating furnace; and
a UV fluorescence analyzer configured to quantitatively analyze the sulfur dioxide in the sulfur dioxide containing gas according to a UV fluorescence method.

7. The device of claim 6, wherein the pure oxygen gas atmosphere comprises at least 99.5 vol. % of oxygen, and the heating furnace is a high-frequency induction heater.

8. The device of claim 6, wherein the means for supplying pure oxygen gas comprises a means for controlling the $O_2$ gas-flow rate.

9. The device of claim 6, further comprising:
a means for measuring a flow rate of the sulfur dioxide containing gas; and
a means for correcting, based on the measured flow rate of the sulfur dioxide containing gas, a quantitative value of sulfur obtained by the UV fluorescence analyzer so as to eliminate an influence of variation in the flow rate of the sulfur dioxide containing gas.

10. The device of claim 7, wherein the means for supplying pure oxygen gas comprises a means for controlling the $O_2$ gas-flow rate.

11. The device of claim 7, further comprising:
a means for measuring a flow rate of the sulfur dioxide containing gas; and
a means for correcting, based on the measured flow rate of the sulfur dioxide containing gas, a quantitative value of sulfur obtained by the UV fluorescence analyzer so as to eliminate an influence of variation in the flow rate of the sulfur dioxide containing gas.

12. The device of claim 8, further comprising:
a means for measuring a flow rate of the sulfur dioxide containing gas; and
a means for correcting, based on the measured flow rate of the sulfur dioxide containing gas, a quantitative value of sulfur obtained by the UV fluorescence analyzer so as to eliminate an influence of variation in the flow rate of the sulfur dioxide containing gas.

13. The method of claim 2, wherein during the heating and combusting the pure oxygen gas is supplied at a flow rate of 4 L/min. to 10 L/min.

14. The method of claim 3, wherein during the heating and combusting the pure oxygen gas is supplied at a flow rate of 4 L/min. to 10 L/min.

15. The method of claim 2, further comprising:
measuring a flow rate of the sulfur dioxide containing gas; and
based on the measured flow rate of the sulfur dioxide containing gas, correcting a quantitative value of sulfur obtained by the analyzing process so as to eliminate an influence of variation in the flow rate of the sulfur dioxide containing gas.

16. The method for analyzing sulfur in a metal sample of claim 3, further comprising:
measuring a flow rate of the sulfur dioxide containing gas; and
based on the measured flow rate of the sulfur dioxide containing gas, correcting a quantitative value of sulfur obtained by the analyzing process so as to eliminate an influence of variation in the flow rate of the sulfur dioxide containing gas.

17. The method for analyzing sulfur in a metal sample of claim 4, further comprising:
measuring a flow rate of the sulfur dioxide containing gas; and
based on the measured flow rate of the sulfur dioxide containing gas, correcting a quantitative value of sulfur obtained by the analyzing process so as to eliminate an influence of variation in the flow rate of the sulfur dioxide containing gas.

* * * * *